(12) United States Patent
Gindelberger

(10) Patent No.: US 8,383,815 B2
(45) Date of Patent: Feb. 26, 2013

(54) HETEROGENEOUS RUTHENIUM METAL CATALYST FOR THE PRODUCTION OF HYDROCODONE, HYDROMORPHONE OR A DERIVATIVE THEREOF

(75) Inventor: David E. Gindelberger, Richmond Heights, MO (US)

(73) Assignee: Mallinckrodt LLC, Hazelwood, MO (US)

( * ) Notice: Subject to any disclaimer, the term of this patent is extended or adjusted under 35 U.S.C. 154(b) by 232 days.

(21) Appl. No.: 12/886,621

(22) Filed: Sep. 21, 2010

(65) Prior Publication Data

US 2011/0071016 A1    Mar. 24, 2011

Related U.S. Application Data

(60) Provisional application No. 61/244,092, filed on Sep. 21, 2009.

(51) Int. Cl.
  *C07D 489/02* (2006.01)
  *C07D 489/00* (2006.01)
(52) U.S. Cl. .......................................... 546/45; 546/44

(58) Field of Classification Search .................... 546/45, 546/44
See application file for complete search history.

(56) References Cited

U.S. PATENT DOCUMENTS

| | | |
|---|---|---|
| 6,589,960 B2 | 7/2003 | Harclerode et al. |
| 7,399,858 B2 | 7/2008 | Wang et al. |
| 7,495,098 B2 | 2/2009 | Tomazi |

FOREIGN PATENT DOCUMENTS

WO    WO-2010/118271 A1 * 10/2010

OTHER PUBLICATIONS

UMA et al., "Transposition of Allylic Alcohols into Carbonyl Compounds Mediated by Transition Metal Complexes", Chem. Rev. 2003, 103, pp. 27-51.

\* cited by examiner

*Primary Examiner* — Charanjit Aulakh

(57) ABSTRACT

The present disclosure generally relates to catalytic methods for producing opioid derivatives. More particularly, the present disclosure relates to the preparation of hydrocodone, hydromorphone, or a derivative thereof, by means of a conversion or an isomerization of codeine, morphine, or a derivative thereof, respectively, using a heterogeneous ruthenium metal catalyst.

21 Claims, No Drawings

HETEROGENEOUS RUTHENIUM METAL CATALYST FOR THE PRODUCTION OF HYDROCODONE, HYDROMORPHONE OR A DERIVATIVE THEREOF

CROSS REFERENCE TO RELATED APPLICATIONS

This application claims the benefit of U.S. Provisional Application No. 61/244,092 filed Sep. 21, 2009, which is incorporated herein in its entirety.

BACKGROUND OF THE DISCLOSURE

The present disclosure generally relates to catalytic methods for producing opioid derivatives. More particularly, the present disclosure relates to the preparation of hydrocodone, hydromorphone, or a derivative thereof, by means of a conversion or an isomerization of codeine, morphine, or a derivative thereof, respectively, using a non-supported, heterogeneous ruthenium metal catalyst.

Hydrocodone and hydromorphone are opiate analgesics having similar qualities to codeine and morphine. Development of new opiate derivatives is desirable to produce new intermediates and potential sources of new analgesics. Conventional methods for producing hydrocodone and hydromorphone typically involve a two step oxidation/reduction route from codeine and morphine, respectively. Unfortunately, these methods can be expensive and inefficient. Attempts to improve efficiency have included the use of catalytic methods. Known catalytic methods include the use of metallic catalysts or complexes, deposited on a support of some kind (e.g., an activated carbon support). However, the preparation of these known catalysts can be difficult. Furthermore, yields are often poor, and isolation of the product is often burdensome. Finally, some catalysts require manufacture and incorporation of expensive supports.

Other known catalytic methods, including the use of finely-divided platinum or palladium in an acidic media, can be environmentally undesirable. Enzymatic methods of conversion have also been attempted. However, like many of the catalysts discussed above, these methods can be costly and difficult to scale up.

Accordingly, a need continues to exist for improved methods for producing various opioids, including hydrocodone, hydromorphone, and derivatives thereof. Desirably, such methods would provide improved yields of the desired reaction product, while enabling the more cost-effective scale up and manufacture of such compounds.

SUMMARY OF THE DISCLOSURE

In view of the foregoing, the present disclosure is directed, in one embodiment, to a method for preparing a compound of Formula II from a compound of Formula I:

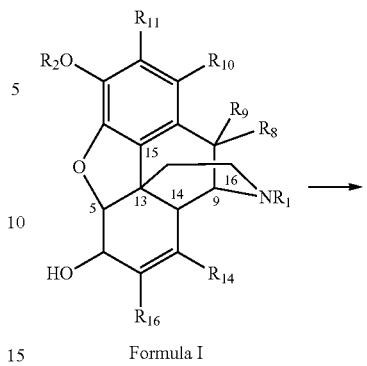

Formula I

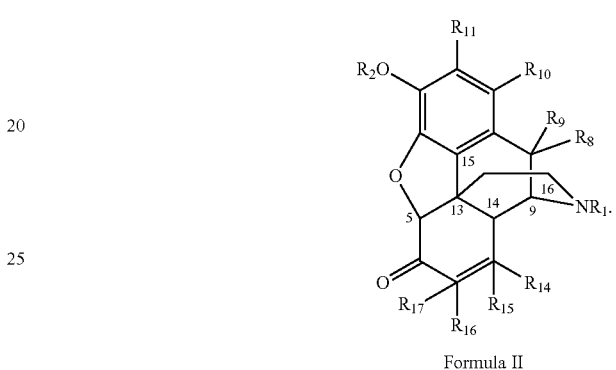

Formula II

The method comprises contacting the compound of Formula I with an acid and a non-supported, heterogeneous ruthenium metal catalyst in a reaction mixture to convert the compound of Formula I to the compound of Formula II, wherein: $R_1$ is selected from the group consisting of hydrogen and substituted or unsubstituted alkyl, substituted or unsubstituted allyl, substituted or unsubstituted cycloalkyl, substituted or unsubstituted aryl, substituted or unsubstituted aryl alkyl, substituted or unsubstituted aryl sulfonyl, substituted or unsubstituted alkyl sulfonyl, substituted or unsubstituted acyl, substituted or unsubstituted formyl, hydroxyl, substituted or unsubstituted carboxyester and substituted or unsubstituted carboxyamide; $R_2$ is selected from the group consisting of hydrogen and substituted or unsubstituted alkyl, substituted or unsubstituted cycloalkyl, substituted or unsubstituted aryl, substituted or unsubstituted aryl alkyl, substituted or unsubstituted acyl, substituted or unsubstituted aryl sulfonyl, substituted or unsubstituted alkyl sulfonyl, substituted or unsubstituted carboxyester, substituted or unsubstituted carboxyamide, substituted or unsubstituted trialkylsilyl, and substituted or unsubstituted heterocycloalkyl; $R_8$ and $R_9$ are independently selected from the group consisting of hydrogen, hydroxyl, substituted or unsubstituted hydrocarbyl, or $R^8$ and $R^9$ together form a carbonyl group; $R_{10}$, $R_{11}$, $R_{14}$ and $R_{15}$ are independently selected from the group consisting of hydrogen, substituted or unsubstituted hydrocarbyl, and a halogen, or $R^{14}$ and $R^{15}$ together form a carbonyl group; and, $R_{15}$ and $R_{17}$ are independently selected from the group consisting of hydrogen, substituted or unsubstituted hydrocarbyl, or $R_{16}$ and $R_{17}$ together form a carbonyl group.

In yet another embodiment, the present disclosure is directed to a method for preparing a compound of Formula IV from a compound of Formula III:

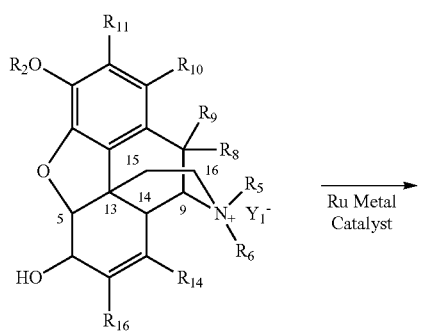

Formula III

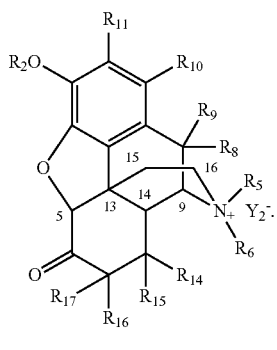

Formula IV

The method comprises contacting the compound of Formula III with an acid and a non-supported, heterogeneous ruthenium metal catalyst in a reaction mixture to convert the compound of Formula III to the compound of Formula IV, wherein: $R_2$ is selected from the group consisting of hydrogen and substituted or unsubstituted alkyl, substituted or unsubstituted aryl, substituted or unsubstituted aryl alkyl, substituted or unsubstituted acyl, substituted or unsubstituted aryl sulfonyl, substituted or unsubstituted alkyl sulfonyl, substituted or unsubstituted carboxyester, substituted or unsubstituted carboxyamide, substituted or unsubstituted trialkylsilyl, and substituted or unsubstituted heterocycloalkyl; $R_5$ and $R_6$ are independently selected from the group consisting of hydrogen and substituted or unsubstituted alkyl, substituted or unsubstituted allyl, substituted or unsubstituted cycloalkyl, substituted or unsubstituted aryl, substituted or unsubstituted aryl alkyl, substituted or unsubstituted aryl sulfonyl, substituted or unsubstituted alkyl sulfonyl, substituted or unsubstituted acyl, substituted or unsubstituted formyl, hydroxyl, substituted or unsubstituted carboxyester and substituted or unsubstituted carboxyamide; $R_8$ and $R_9$ are independently selected from the group consisting of hydrogen, hydroxyl, substituted or unsubstituted hydrocarbyl, or $R^8$ and $R^9$ together form a carbonyl group; $R_{10}$, $R_{11}$, $R_{14}$ and $R_{15}$ are independently selected from the group consisting of hydrogen, substituted or unsubstituted hydrocarbyl, and a halogen, or $R^{14}$ and $R^{15}$ together form a carbonyl group; $R_{16}$ and $R_{17}$ are independently selected from the group consisting of hydrogen, substituted or unsubstituted hydrocarbyl, or $R_{16}$ and $R_{17}$ together form a carbonyl group; and, $Y_1$ and $Y_2$ are each an anion, which may be the same or different.

In yet another embodiment, the present disclosure is directed to one or both of the foregoing methods, wherein the method further comprises: (i) isolating the non-supported, ruthenium metal catalyst from the reaction mixture; (ii) contacting the isolated, non-supported ruthenium metal catalyst with a solution in which the catalyst is at least partially soluble, the solution comprising a base and a hypochlorite, in order to increase the activity of the catalyst; and, (iii) preparing a subsequent reaction mixture comprising the activated, non-supported ruthenium metal catalyst and a compound of Formula I, or Formula III. Optionally, the isolated, non-supported catalyst may be washed with an aqueous alcoholic solution, prior to being contacted with the solution in which the catalyst is at least partially soluble.

In yet another embodiment, the present disclosure is directed to a method for regenerating a non-supported, ruthenium metal catalyst. The method comprises contacting the non-supported ruthenium metal catalyst with a solution in which the catalyst is at least partially soluble, the solution comprising a base and a hypochlorite, in order to increase the activity of the catalyst. Optionally, the non-supported catalyst may be washed with an aqueous alcoholic solution, prior to being contacted with the solution in which the catalyst is at least partially soluble.

It is to be noted that one or more of the additional features detailed below may be incorporated into one or more of the above-noted embodiments, without departing from the scope of the present disclosure.

DETAILED DESCRIPTION OF THE DISCLOSURE

In accordance with the present disclosure, it has been discovered that a ruthenium metal catalyst and, more particularly, a non-supported heterogeneous ruthenium metal catalyst may be used in a method for producing opioid derivatives. In one or more preferred embodiments, the catalyst may be used in the preparation of hydrocodone, hydromorphone, or a derivative thereof, by means of a catalyzed isomerization of codeine, morphine, or a derivative thereof, respectively.

The catalysts detailed herein have been found to possess high activity toward such isomerization reactions. As an illustration, and therefore not to be viewed in a limiting sense, in various embodiments a conversion of at least about 85 mole %, at least about 90 mole %, at least about 95 mole %, at least about 98 mole % or more may be achieved in accordance with the methods of the present disclosure, ultimately leading to a compound having a purity of at least at least about 90 mole %, at least about 95 mole %, at least about 98 mole % or more (as determined by means generally known in the art).

Additionally, the catalysts of the present disclosure are advantageously heterogeneous, allowing for the efficient recovery and reuse of the catalyst, as further detailed elsewhere herein.

In this regard it is to be noted that "ruthenium metal catalyst" refers to a ruthenium-containing catalyst that is not part of a metal-ligand complex, and additionally is not deposited on a support (i.e., is "non-supported"). In one particular embodiment, the ruthenium metal catalyst is elemental ruthenium, such as for example ruthenium black.

1. OPIOID STARTING MATERIALS AND ISOMERIZATION PRODUCTS

In one embodiment of the present disclosure, a compound of Formula I may be contacted with a non-supported, heterogeneous ruthenium metal catalyst in a conversion or an isomerization reaction to produce a compound of Formula II:

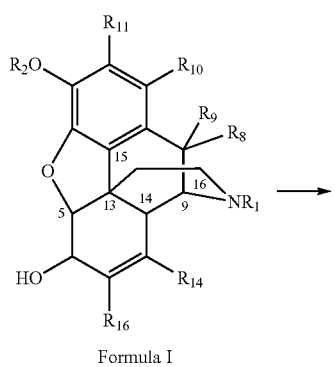

Formula I

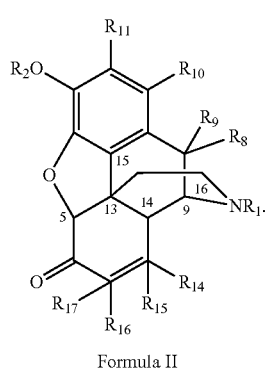

Formula II

In the structures, $R_1$ may be selected from, for example, hydrogen and substituted or unsubstituted alkyl, substituted or unsubstituted allyl, substituted or unsubstituted cycloalkyl, substituted or unsubstituted aryl, substituted or unsubstituted aryl alkyl, substituted or unsubstituted aryl sulfonyl, substituted or unsubstituted alkyl sulfonyl, substituted or unsubstituted acyl, substituted or unsubstituted formyl, hydroxyl, substituted or unsubstituted carboxyester and substituted or unsubstituted carboxyamide. Additionally, $R_2$ may be selected from, for example, hydrogen and substituted or unsubstituted alkyl, substituted or unsubstituted cycloalkyl, substituted or unsubstituted aryl, substituted or unsubstituted aryl alkyl, substituted or unsubstituted acyl, substituted or unsubstituted aryl sulfonyl, substituted or unsubstituted alkyl sulfonyl, substituted or unsubstituted carboxyester, substituted or unsubstituted carboxyamide, substituted or unsubstituted trialkylsilyl and substituted or unsubstituted heterocycloalkyl. $R_8$ and $R_9$ may be independently selected from the group consisting of hydrogen, hydroxyl, hydrocarbyl and substituted hydrocarbyl. Alternatively, $R_8$ and $R_9$ may together form a carbonyl group. $R_{10}$, $R_{11}$, $R_{14}$ and $R_{15}$ may independently be selected from the group consisting of hydrogen, substituted or unsubstituted hydrocarbyl, and a halogen. Alternatively, $R_{14}$ and $R_{15}$ may together form a carbonyl group. $R_{16}$ and $R_{17}$ may independently be selected from the group consisting of hydrogen, and substituted or unsubstituted hydrocarbyl. Alternatively, $R_{16}$ and $R_{17}$ may together form a carbonyl group.

In some embodiments of the present disclosure, $R_1$ may be selected from the group consisting of hydrogen, and —OCOR$_3$, and R$_3$ may be substituted or unsubstituted hydrocarbyl. In such embodiments, $R_2$ may in one particular embodiment be selected from the group consisting of hydrogen and methyl.

In several particular embodiments, $R_1$ is methyl and $R_2$ is methyl or H. In such embodiments, all other R groups (i.e., $R_8$, $R_9$, $R_{10}$, $R_{11}$, $R_{14}$, $R_{15}$, $R_{16}$ and $R_{17}$) may be hydrogen; that is, Formula I may be codeine or morphine, respectively, leading to the formation of hydrocodone or hydromorphone, respectively. Stated differently, the conversion or isomerization reaction may be carried out to convert a compound of Formula IA to a compound of Formula IIA, or it may be carried out to convert a compound of Formula IB to a compound of Formula IIB, as illustrated below:

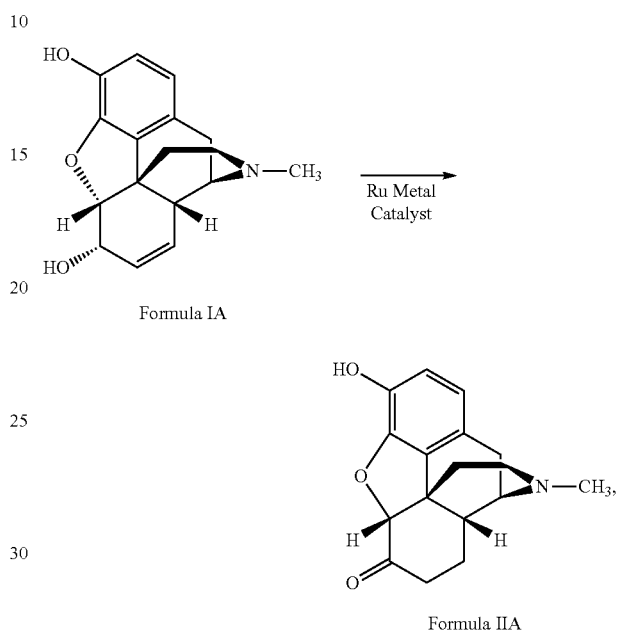

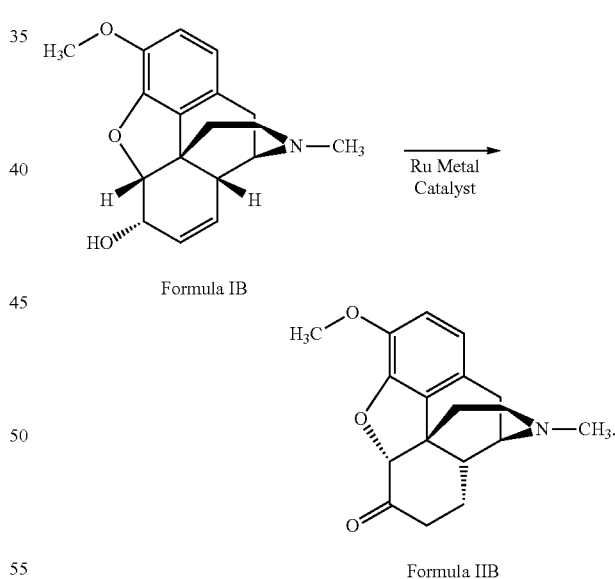

In certain embodiments, the compounds of Formula I and II may be in the stereochemical form of the (+)-enantiomer. In such embodiments, the stereochemistry of the C(5), C(13), C(14), and C(9) carbons, respectively, of each compound may be selected from the group consisting of a combination listed in Table A, below (wherein the C(5), C(13), C(14), and C(9) carbon atoms are as noted in the structures of Formulas I and II). In such enantiomer structures, both the C(15) and the C(16) atoms may be either on the alpha face of the molecule or the beta face of the molecule.

TABLE A

Stereoisometric Combinations for C(5), C(13),
C(14), and C(9) Carbon Atoms of Formula I and Formula II

| Combination | C5 | C13 | C14 | C9 |
|---|---|---|---|---|
| 1 | R | R | R | R |
| 2 | R | R | S | R |
| 3 | R | R | R | S |
| 4 | R | R | S | S |
| 5 | R | S | R | R |
| 6 | R | S | S | R |
| 7 | R | S | R | S |
| 8 | R | S | S | S |
| 9 | S | R | R | R |
| 10 | S | R | S | R |
| 11 | S | R | R | S |
| 12 | S | R | S | S |
| 13 | S | S | R | R |
| 14 | S | S | S | R |
| 15 | S | S | R | S |
| 16 | S | S | S | S |

In an alternative embodiment of the present disclosure, the reactant or starting compounds and/or reaction products may be in the form quaternary amine (or ammonium) salts. For example, in such an embodiment, a compound of Formula III may be contacted with a non-supported, heterogeneous ruthenium metal catalyst in a conversion or an isomerization reaction to produce a compound of Formula IV:

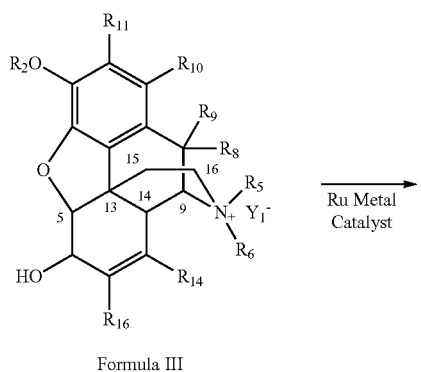

Formula III

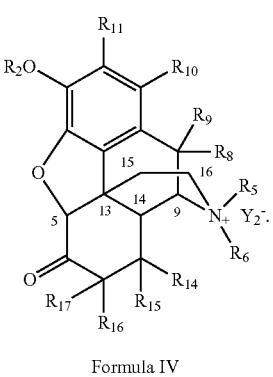

Formula IV

In the structures, $R_2$, $R_8$-$R_{11}$ and $R_{14}$-$R_{17}$ are as defined above, while $R_5$ and $R_6$ may be, for example, independently selected from hydrogen, and substituted or unsubstituted alkyl, substituted or unsubstituted aryl, substituted or unsubstituted aryl alkyl, substituted or unsubstituted acyl, substituted or unsubstituted aryl sulfonyl, substituted or unsubstituted alkyl sulfonyl, substituted or unsubstituted carboxyester and substituted or unsubstituted carboxyamide. $Y_1$ and $Y_2$ are anions, each independent selected from, for example, a halogen ion (e.g., $Cl^-$, $F^-$, $Br^-$, $I^-$), as well as $H^-$, $BF_4^-$, $PF_6^-$, $ClO_4^-$, $CHO_2^-$, $CF_3CO_2^-$, $CF_3SO_3^-$, $CH_3CO_2^-$, $ArCO_2^-$, $CH_3SO_3^-$, p-tolyl$SO_3^-$, $HSO_4^-$ and $H_2PO_4^-$. It is to be noted that $Y_1$ and $Y_2$ may be the same or different.

It is to be further noted that while the starting compounds and isomerization reaction product compounds illustrated above have the same base or core structure (i.e., a fused, tetracyclic structure), the methods of the present disclosure may be used with essentially any alkaloid having an allyl alcohol functionality. Additionally, or alternatively, it is to be noted that, like the structures of Formulas I and II, the process of the present disclosure may be used to prepare the (+)-enantiomers of Formulas III and/or IV.

While the base or core structure of the compounds illustrated above has a specific arrangement of substituents, additional substituents and/or different substituents may be present at one or more sites therein without departing from the scope of the present disclosure, provided the substituted structure remains an alkaloid having an allyl alcohol functionality therein. Accordingly, the structures illustrated in, for example, Formulas I through IV above should not be viewed in a limiting sense.

It is to be noted that the starting compounds referenced herein, such as those of Formula I and Formula III, and in particular the compounds of Formula IA and Formula IB, may be obtained commercially, and/or may be prepared according to methods generally known in the art, including for example the methods disclosed in U.S. Pat. No. 7,495,098, the entire contents of which are incorporated herein by reference for all relevant and consistent purposes.

2. RUTHENIUM METAL CATALYSTS

In accordance with the present disclosure, a compound (such as a compound of Formula I, IA, IB, and Formula III) is contacted with a ruthenium metal catalyst. As previously noted, the ruthenium metal catalyst is not supported; that is, the ruthenium metal does not form part of a ligand-complex and is not supported on a conventional catalyst support such as a zeolite, alumina, silica, carbon, or the like.

Also as previously noted, the ruthenium metal catalyst contains elemental ruthenium; that is, the catalyst is ruthenium metal having an average oxidation state of 0. It is to be further noted that the ruthenium metal catalyst of the present disclosure may contain any combination of the naturally occurring stable isotopes of ruthenium and may also be characterized by a number of different crystal lattice configurations, without departing from the scope of the present disclosure.

In certain embodiments, the elemental ruthenium metal catalyst is in the form of at least one of ruthenium black and a ruthenium sponge. Ruthenium black and ruthenium sponges may be produced by any of the methods known by those of ordinary skill in the art and may be obtained from commercial suppliers such as, for example, Colonial Metals, Inc. (Elkton, Md.) or from Sigma-Aldrich (St. Louis, Mo.).

In embodiments of methods of the present disclosure, the ruthenium metal catalyst may be combined with a compound of Formula I (including IA and IB), or Formula III, to form a reaction mixture. Other catalysts materials may be included within the reaction mixture and some catalysts materials (e.g., other metals) may be included in the ruthenium metal catalyst composition itself without departing from the scope of the present disclosure. For instance, ruthenium may be alloyed or mixed with another metal such as, for example, platinum, nickel or palladium. The purity of the non-supported, ruthenium metal catalyst (i.e., the weight concentration of the catalyst material that is ruthenium metal) may be at least about 50%; that is, the catalyst of the present disclosure may contain at least about 50% (by weight, based on the total weight of the catalyst) ruthenium metal. In alternative embodiments, however, the catalyst may have a ruthenium metal concentration of at least about 75%, at least about 90%, at least about 95%, at least about 99% or even at least about 99.9% (by weight, based on the total weight of the catalyst). Accordingly, in one or more embodiments of the present disclosure, the catalyst may consist of, or consist essentially of, ruthenium metal (e.g., elemental ruthenium, such as ruthenium black).

The ruthenium metal catalyst may be in the form of a powder. In such embodiments, the powder may have, for example, an average particle size of from greater than about 1 micron to less than about 800 microns, or about 40 microns to about 700 microns, or from about 75 microns to about 300 microns, while in alternative embodiments the powder may have an average particle size that is much smaller, the size being for example from tens of nanometers (e.g., at least about 10, about 25, about 50, about 75 nanometers or more) up to hundreds of nanometers (e.g., about 100, about 250, about 500, about 750 nanometers or more). Additionally, or alternative, in these or other embodiments, the ruthenium metal catalyst (e.g., ruthenium powder or ruthenium sponge) may have an average surface area of at least about 5 $m^2/g$, at least about 10 $m^2/g$, at least about 15 $m^2/g$, at least about 20 $m^2/g$, at least about 25 $m^2/g$, at least about 30 $m^2/g$, at least about 35 $m^2/g$, or at least about 40 $m^2/g$ (the surface area, for example, being within the range of about 5 and about 40 $m^2/g$, or about 10 to about 30 $m^2/g$, or about 15 to about 25 $m^2/g$).

One or more of the catalysts described herein may optionally be made more active than the commercially available catalyst prior to contact with the reaction starting materials (e.g., obtained in activated form ready for use), or may be activated as part of the reaction process (i.e., obtained in an inactive form and activated prior to or concurrently with the isomerization reaction). For example, in one or more embodiments herein the catalyst may be contacted with a solution in which the catalyst is at least partially soluble to increase the activity of the catalyst. One particularly suitable solution includes diluted hypochlorite. The use of hypochlorite solutions is more fully described below under the section entitled "Regeneration of the Ruthenium Metal Catalyst."

3. ISOMERIZATION OR CONVERSION REACTION

Generally speaking, the desired reaction product may be formed using the ruthenium metal catalyst of the present disclosure in combination with reaction conditions known in the art. More particularly, however, the conversion or isomerization reaction may be performed according to methods generally known in the art, which involve contacting a starting compound as detailed herein (i.e., a compound of Formula I, IA, IB, or III) with an acid and a catalyst of the present disclosure. An exemplary method includes contacting (e.g., dissolving or suspending) the starting compound in a suitable solvent, and a suitable acid, in a reaction vessel. Suitable solvents may be selected from, for example, water and other water-miscible co-solvents. Suitable water-miscible co-solvents may be selected from, for example, acetone, $C_1$ to $C_{10}$ alcohols (e.g., ethanol and methanol), and various ethers (e.g., diethyl ether). Suitable acids for use in the reaction mixture include sulfuric acid, alkyl sulfuric acid, aryl sulfuric acid, hydrochloric acid, acetic acid and mixtures thereof.

In this regard it is to be noted that the reaction may proceed to completion in one step or; stated differently, compounds of Formula II, IIA, IIB and IV are produced from compounds of Formula I, IA, IB and Formula III, respectively, without formation and/or isolation of intermediate compounds. Additionally, or alternatively, the reaction may be carried out in a single reaction vessel; that is, the process of the present disclosure may be a "one-pot" reaction process.

The reaction vessel may be flushed with an inert atmosphere, such as argon or nitrogen, prior to the addition of the catalyst thereto; however, the reaction may proceed with suitable conversion under an ambient atmosphere (i.e., under air). The reaction mixture may be refluxed, optionally under the inert atmosphere, until the isomerization reaction (or conversion) is essentially complete (as determined using means generally known in the art, such as for example HPLC or TLC, to analyze or measure the concentration of the desired reaction product, and/or the starting compound, in the reaction mixture). The reaction vessel may be maintained at atmospheric pressure; however, other pressures may be used without limitation.

Typically, the molar amount of catalyst added to the reaction (or reaction mixture) may be at least about 1 mole % and less than about 20 mole % of the starting compound (e.g., the compounds of Formula I, IA, IB, or III). For instance, the molar amount of catalyst added to the reaction mixture may be at least about 1 mole % and less than about 20 mole %, or at least about 5 mole % and less than about 15 mole %, or at least about 8 mole % and less than about 12 mole %, based on the amount of the compound of Formula I (or IA, IB, or III) present therein. In this regard it is to be noted, however, that the mole % of the catalyst may be altered as needed in order to optimize yield or conversion, and/or purity, of the desired reaction product. For example, in one preferred embodiment, the molar amount of catalyst added to the reaction mixture is about 10 mole %. Accordingly, the ranges provided herein are for illustration, and therefore should not be viewed in a limiting sense.

The duration and/or reaction temperature may also be altered in order to optimize yield or conversion, and/or purity, of the desired reaction product. Typically, however, the reaction is allowed to continue for at least about 30 minutes and may continue for about 24 hours or more, although in various alternative embodiments the reaction may be allowed to continue for at least about 1 hour, about 4 hours, about 8 hours, or about 12 hours. In various embodiments, the reaction may be allowed to continue for between about 4 and less than about 24 hours, or about 8 and less than about 22 hours, or about 12 and less than about 20 hours. In these or yet other alternative embodiments, the reaction mixture may be maintained at a temperature of greater than about 25° C. and less than about 150° C., or from about 50° to about 120° C., or from about 75° C. to about 100° C. In some suitable embodiments, the reaction mixture is maintained above about the reflux temperature of the reaction mixture.

Like the reaction duration and/or reaction temperature, the amount of acid in the reaction mixture may be altered in order to optimize yield or conversion, and/or purity, of the desired reaction product. Typically, however, the amount of acid in the reaction mixture per mole of starting compound may be from about 0.5 and about 3 moles of acid per mole of the starting compound and, in other embodiments, from about 0.75 to about 2.5 moles, or from about 1 to about 2 moles of acid per mole of starting compounds present therein. Additionally, or alternatively, the concentration of acid in the reaction mixture may be adjusted or controlled such that the concentration is about 1 g of acid per about 2 to about 20 ml of solvent in the reaction mixture, or about 1 g of acid per about 3 to about 15 ml of solvent in the reaction mixture, about 1 g of acid per about 4 to about 10 ml of solvent in the reaction mixture.

The concentration of alcohol in the reaction mixture may be at least about 1 ml per gram of starting compounds, and in some embodiments may be at least about 2, about 3, about 4 or about 5 ml per gram. For example, the concentration of water-miscible solvent (e.g., alcohol) may be from about 0.5 to about 10 ml per gram of starting compounds, from about 1 to about 5 ml per gram of starting compounds, or from about 2 to about 4 ml per gram of starting compounds.

The concentration of water in the reaction mixture may be at least about 1 ml per gram of starting compounds and, in other embodiments may be at least about 2, about 3, about 4 or about 5 ml per gram. For example, the concentration of water may be from about 0.5 to about 10 ml per gram of starting compounds, from about 1 to about 5 ml per gram of starting compounds, or from about 2 to about 4 ml per gram of starting compounds.

Accordingly, in various embodiments the ratio of water to water-miscible solvent in the reaction mixture may be from about 1:20 to about 20:1, or about 1:10 to about 10:1, about 1:5 to about 5:1, from about 1:3 to about 3:1, from about 1:2 to about 2:1, or from about 1:1.5 to about 1.5:1. In one particular embodiment, however, the ratio of water to water-miscible solvent is about 1:1. It should be understood that other amounts and concentrations of acid, water and water-miscible solvent may be used in the reaction mixture without departing from the scope of the present disclosure.

In various embodiments, a conversion of at least about 85 mole %, at least about 90 mole %, at least about 95 mole %, at least about 98 mole % or more may be achieved in accordance with the method of the present disclosure, ultimately leading to a compound having a purity of at least about 90 mole %, at least about 95 mole %, at least about 98 mole % or more (as determined by means generally known in the art), after isolation and purification of the reaction product (using means generally known in the art).

After the reaction has reached a desired point of completion (determined as noted above), the mixture may be cooled as needed and the reaction product isolated using methods generally known in the art (e.g., filtration, centrifugation, crystallization, etc.). Once isolated, the reaction product may be further purified if needed, again using methods generally known in the art (e.g., purified by recrystallization in a suitable solvent as is well known in the art, or by any other conventional methods of purification). In some embodiments, the concentration of ruthenium in the product may be controlled to be less than about 12 ppm, less than about 10 ppm, less than about 8 ppm, less than about 6 ppm, less than about 4 ppm, less than about 2 ppm, or even less than about 1 ppm by weight.

The isomerization or conversion reactions of the present disclosure may be carried out in continuous or batch form. The catalyst of the present disclosure may, for example, be placed in a column or container as part of a loop reactor. A solution containing compounds of Formula I, IA, IB or III may be pumped or gravity fed through a catalyst bed and cycled back to the reactor until the desired conversion to a compound of Formula II, IIA, IIB or IV, respectively, is produced. This allows many cycles (perhaps several batches) of product to be obtained with a given bed. Upon cooling, the product may crystallize out of reaction solution in high purity, to be recovered by filtration or centrifugation.

4. REGENERATION OF THE RUTHENIUM METAL CATALYST

The present process is advantageous for a number of reasons, including the fact that after the reaction has reached its desired completion, the catalyst may be easily recovered and reused, because the catalyst exhibits little or no solubility in the reaction mixture; that is, little or no catalyst is dissolved in the reaction mixture. The non-supported, heterogeneous ruthenium catalyst may be recovered by known means (e.g., filtering, decanting and the like) and prepared for reuse in a subsequent reaction mixture. Once the heterogeneous catalyst has been isolated from the reaction mixture, it may optionally be washed in an aqueous solution to clean the catalyst and to remove any impediments to active sites within the catalyst. The aqueous solution may include other compounds, such as an alcohol, to assist in cleaning the catalyst.

Prior to or after the optional washing of the catalyst with an aqueous solution, the catalyst may be contacted with a solution in which the catalyst is partially soluble, to increase the activity of the catalyst (i.e., a "catalyst-soluble solution"). Suitable catalyst-soluble solutions include those containing a hypochlorite (e.g., sodium hypochlorite), as well as optionally a base (e.g., an alkali metal or alkaline earth-metal hydroxide, such as potassium or sodium hydroxide). Typically, about 1 gram of the catalyst is washed in about 20, about 25 or about 30 ml of catalyst-soluble solution, the solution comprising about 20 to about 25 ml of a base solution (e.g., a KOH solution, the KOH concentration therein being about 0.05 to about 0.25 N, or about 0.1 to about 0.2 N), and about 2.5 to about 5 ml of a hypochlorite solution (e.g., a NaOCl solution, the NaOCl concentration therein being about 1 to about 10 wt %, or about 2 to about 8 wt %, or about 4 to about 6 wt %). Accordingly, in various embodiments the catalyst-soluble solution may have an overall hypochlorite concentration of from about 0.05 wt % to about 6 wt %, from about 0.1 wt % to about 4 wt %, or from about 0.5 wt % to about 2 wt %. The overall concentration of base in the catalyst-soluble solution may be from 0.05 wt % to about 10 wt %, from about 0.1 wt % to about 5 wt %, or from about 0.25 wt % to about 2.5 wt %. In this regard it is to be noted, however, that the components of the catalyst-soluble solution, and/or the concentration of the components or the catalyst therein, may be other than herein described without departing from the scope of the present disclosure.

The amount of ruthenium that dissolves in the partially-soluble solution may be less than about 15%, about 10%, about 5% or even about 1%, based on weight, of the ruthenium that contacts the solution; that is, at least about 85 wt %, about 90 wt %, about 95 wt %, or even about 99 wt % of the catalyst that is subjected to the cleaning solution or step is recovered. For instance, in various embodiments, the amount of ruthenium that is dissolved in the catalyst-soluble solution may be from about 1% to about 15%, or from about 1% to 10%, or from about 1% to 5%, by weight of the catalyst exposed thereto.

In these or other embodiments, the washed, non-supported ruthenium metal catalyst is contacted with the catalyst-soluble solution for at least about 30 seconds, at least about 1 minute, at least about 2 minutes, or at least about 3 minutes, and less than about 10 minutes, about 8 minutes, about 6 minutes, or even about 5 minutes, the contact period being for example within the range of about 30 seconds to about 10 minutes, or from about 1 minute to about 8 minutes, or about 2 minutes to about 6 minutes, or about 3 minutes to about 5 minutes. Additionally, the catalyst-soluble solution may be maintained at a temperature from about 0° C. to about 100°

C., from about 5° C. to about 75° C., from about 15° C. to about 50° C., or even at about room temperature, during the catalyst regeneration step.

After the non-supported, ruthenium metal catalyst has been contacted with the noted catalyst soluble solution, the catalyst may be isolated therefrom (by, for example, filtration), washed one or more times with water, and then used again in the process of the present disclosure.

5. DEFINITIONS

The compounds described herein may have asymmetric centers. Compounds of the present disclosure containing an asymmetrically substituted atom may be isolated in optically active or racemic form. All chiral, diastereomeric, racemic forms and all geometric isomeric forms of a structure are intended, unless the specific stereochemistry or isomeric form is specifically indicated. All processes used to prepare compounds of the present disclosure and intermediates made therein are considered to be part of the present disclosure.

As used herein, "optional" or "optionally" means that the subsequently described event or circumstance may or may not occur, and that the description includes instances where the event or circumstance occurs and instances where it does not.

The terms "aryl" or "ar" as used herein, alone or as part of another group, denote optionally substituted homocyclic aromatic groups, preferably monocyclic or bicyclic groups containing from 6 to 12 carbons in the ring portion, such as phenyl, biphenyl, naphthyl, substituted phenyl, substituted biphenyl or substituted naphthyl. Phenyl and substituted phenyl are the more preferred aryl.

The terms "halogen" or "halo" as used herein alone or as part of another group refer to chlorine, bromine, fluorine, and iodine.

Unless otherwise indicated, the "alkyl" groups described herein are preferably lower alkyl containing from one to about 10 carbon atoms in the principal chain, and up to about 20 carbon atoms. They may be straight or branched chain or cyclic (e.g., cycloalkyl) and include methyl, ethyl, propyl, isopropyl, butyl, pentyl, hexyl and the like. Accordingly, the phrase "$C_{1-20}$ alkyl" generally refers to alkyl groups having between about 1 and about 20 carbon atoms, and includes such ranges as about 1 to about 15 carbon atoms, about 1 to about 10 carbon atoms, or about 1 to about 5 carbon atoms, while the phrase "$C_{1-10}$ alkyl" generally refers to alkyl groups having between about 1 and about 10 carbon atoms, and includes such ranges as about 1 to about 8 carbon atoms, or about 1 to about 5 carbon atoms.

The term "substituted" as in "substituted aryl" or "substituted alkyl" and the like, means that in the group in question (i.e., the aryl, the alkyl, or other moiety that follows the term), at least one hydrogen atom bound to a nitrogen atom or carbon atom, respectively, is replaced with one or more substituent groups such as hydroxy, alkoxy, amino, halo, and the like. When the term "substituted" introduces a list of possible substituted groups, it is intended that the term apply to every member of that group. That is, the phrase "substituted alkyl, aryl, acyl, etc." is to be interpreted as "substituted alkyl, substituted aryl, and substituted acryl", respectively. Similarly, "optionally substituted alkyl, aryl and acyl" is to be interpreted as "optionally substituted alkyl, optionally substituted aryl and optionally substituted acyl."

The modifiers "hetero", as in "heterocycle" refer to a molecule or molecular fragment in which one or more carbon atoms is replaced with a heteroatom. Thus, for example, the term "heteroalkyl" refers to an alkyl group that contains a heteroatom, while "heterocycloalkyl" reference to a cycloalkyl group that contains a heteroatom. When the term "heteroatom-containing" introduces a list of possible heteroatom-containing groups, it is intended that the term apply to every member of that group.

As illustrated below, the term "fused, tetracyclic" generally refers to a compound that includes four rings therein, and further wherein each of the rings in the compound share two ring atoms (e.g., carbon atoms or heteroatoms, as highlighted by the dashed-circles below). Optionally, when a heteroatom is present, the "fused hetero-tetracyclic" may be used.

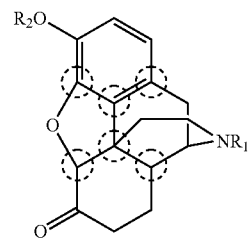

Having described the disclosure in detail, it will be apparent that modifications and variations are possible without departing from the scope of the disclosure defined in the appended claims.

EXAMPLES

The following non-limiting examples are provided to further illustrate the present disclosure.

Example 1

Preparation of Hydromorphone from Morphine Using Ruthenium Black

A cylindrical jacketed reactor (300 ml) with a bottom out valve was used for the reaction. The reactor had a 4-neck head equipped with $N_2$ inlet, thermocouple, overhead mixer and Claisen plus condenser capped with a bubbler. The reaction was conducted under a nitrogen atmosphere. The reactor was charged with wet morphine (13.96 g; 72 wt % being active morphine), ruthenium black (0.356 g), water (30 ml), ethanol (30 ml) and sulfuric acid (3.82 g). The jacket temperature was set to 85° C. and the mixture was stirred. The internal temperature was maintained at about 75° C. throughout the run and until the reaction was determined to be complete by thin layer chromatography (TLC). The TLC solvent was 98:2 methanol to $NH_4OH$ by volume. The mixture was stirred 16 hours then cooled and filtered. Filtering produced 0.332 g of ruthenium black. HPLC analysis of mother liquors showed >99% consumption of morphine and 97% conversion to hydromorphone.

Example 2

Preparation of Hydrocodone from Codeine Using Ruthenium Black

A glass flask (20 ml) was charged with codeine (1.99 g), ruthenium black (0.067 g), water (5 ml), ethanol (5 ml) and sulfuric acid (0.72 g). The mixture was stirred and the temperature was raised to the reflux temperature. The reflux temperature was maintained until the reaction was complete as determined by TLC with the TLC solvent being 98:2 ethanol to NH₄OH by volume. This mixture was stirred for 20 hours and then cooled and filtered. 0.062 g of ruthenium was recovered. HPLC analysis of mother liquors showed 96% conversion to hydrocodone.

Example 3

Preparation of Hydromorphone from Morphine Using Regenerated Catalyst

A cylindrical jacketed reactor (300 ml) with a bottom out valve was used to conduct the reaction. The reactor had a 4-neck head equipped with N₂ inlet, thermocouple, overhead mixer and Claisen plus condenser capped with a bubbler. The reaction proceeded under a nitrogen atmosphere. The reactor was charged with wet morphine (12.81 g; with 72 wt % being active), ruthenium black (0.355 g), water (50 ml), ethanol (50 ml) and sulfuric acid (3.60 g). The ruthenium black was previously used in a reaction mixture and was recovered and regenerated by washing with a dilute hypochlorite solution (0.56 wt % sodium hydroxide; 1.2 wt % hypochlorite) followed by washing with water.

The jacket temperature was set to 90° C. and the mixture was stirred. The internal temperature remained about 80° C. throughout the run. The reflux temperature was maintained until the reaction is complete by TLC. The TLC solvent was 98:2 methanol to NH₄OH by volume. This mixture was stirred for 4 hours and then cooled and filtered to recover 0.282 g of ruthenium. HPLC analysis of mother liquors showed >99% consumption of morphine and 98% conversion to hydromorphone.

Example 4

Regeneration of a Heterogeneous Ruthenium Catalyst

Previously used ruthenium black (0.333 g) was suspended in 4 ml KOH (0.1 N) containing 0.5 ml hypochlorite solution (6 wt %). The mixture was stirred for 5 minutes then filtered. The solids are washed with 2 ml of water and 1 ml of ethanol. The solids were briefly air dried giving a quantitative yield of reactivated ruthenium black. The resulting solids typically showed activity higher than the fresh, unused ruthenium black. Without the wash, the activity was typically zero on recycle attempts.

When introducing elements of the present disclosure or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

As various changes could be made in the above apparatus and methods without departing from the scope of the disclosure, it is intended that all matter contained in the above description and shown in the accompanying figures shall be interpreted as illustrative and not in a limiting sense.

What is claimed is:

1. A method for preparing a compound of Formula II from a compound of Formula I:

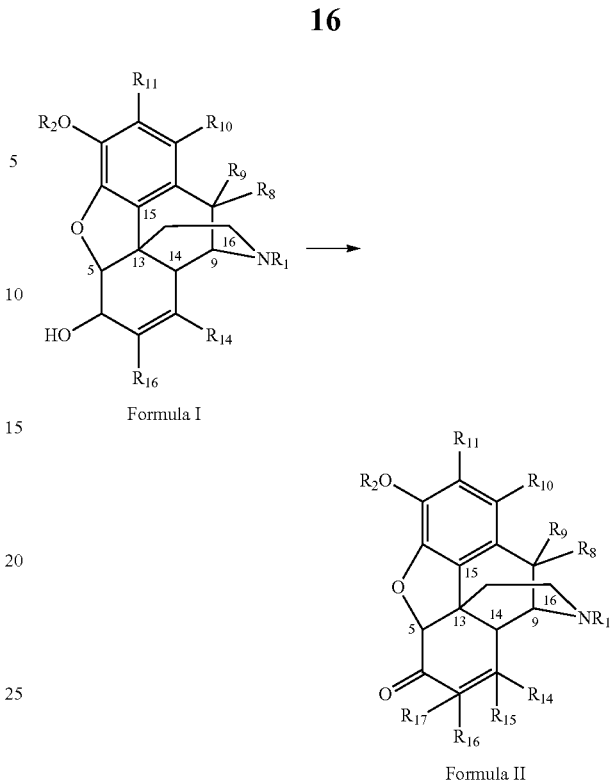

Formula I

Formula II the method comprising contacting the compound of Formula I with an acid and a non-supported, heterogeneous ruthenium metal catalyst in a reaction mixture to convert the compound of Formula I to the compound of Formula II, wherein:

$R_1$ is chosen from hydrogen and substituted or unsubstituted alkyl, substituted or unsubstituted allyl, substituted or unsubstituted cycloalkyl, substituted or unsubstituted aryl, substituted or unsubstituted aryl alkyl, substituted or unsubstituted aryl sulfonyl, substituted or unsubstituted alkyl sulfonyl, substituted or unsubstituted acyl, substituted or unsubstituted formyl, hydroxyl, substituted or unsubstituted carboxyester and substituted or unsubstituted carboxyamide;

$R_2$ is chosen from hydrogen and substituted or unsubstituted alkyl, substituted or unsubstituted cycloalkyl, substituted or unsubstituted aryl, substituted or unsubstituted aryl alkyl, substituted or unsubstituted acyl, substituted or unsubstituted aryl sulfonyl, substituted or unsubstituted alkyl sulfonyl, substituted or unsubstituted carboxyester, substituted or unsubstituted carboxyamide, substituted or unsubstituted trialkylsilyl, and substituted or unsubstituted heterocycloalkyl;

$R_8$ and $R_9$ are independently chosen from hydrogen, hydroxyl, substituted or unsubstituted hydrocarbyl, or $R_8$ and $R_9$ together form a carbonyl group;

$R_{10}$, $R_{11}$, $R_{14}$ and $R_{15}$ are independently chosen from hydrogen, substituted or unsubstituted hydrocarbyl, and a halogen, or $R_{14}$ and $R_{15}$ together form a carbonyl group; and, $R_{16}$ and $R_{17}$ are independently chosen from hydrogen, substituted or unsubstituted hydrocarbyl, or $R_{16}$ and $R_{17}$ together form a carbonyl group.

2. The method of claim 1, wherein $R_1$ is chosen from hydrogen, methyl and —OCOR₃, and further wherein $R_3$ is substituted or unsubstituted hydrocarbyl and wherein $R_2$ is chosen from hydrogen and methyl.

3. The method of claim 1, wherein the compounds of Formula I and II are (+)-enantiomers, and the stereochemistry of the C(5), C(13), C(14), and C(9) carbons, respectively, of each compound is chosen from a combination listed in Table A, below, provided that the C(15) and the C(16) atoms are both either on the alpha face of the molecule or the beta face of the molecule:

TABLE A

| Combination | C5 | C13 | C14 | C9 |
|---|---|---|---|---|
| 1 | R | R | R | R |
| 2 | R | R | S | R |
| 3 | R | R | R | S |
| 4 | R | R | S | S |
| 5 | R | S | R | R |
| 6 | R | S | S | R |
| 7 | R | S | R | S |
| 8 | R | S | S | S |
| 9 | S | R | R | R |
| 10 | S | R | S | R |
| 11 | S | R | R | S |
| 12 | S | R | S | S |
| 13 | S | S | R | R |
| 14 | S | S | S | R |
| 15 | S | S | R | S |
| 16 | S | S | S | S |

4. The method of claim 1, wherein:

(a) the conversion reaction is carried out to convert the compound of Formula IA to the compound of Formula IIA; or

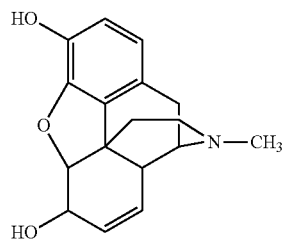

Formula IA

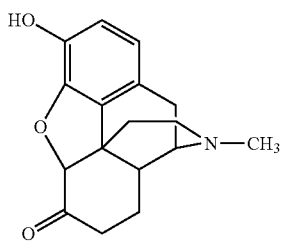

Formula IIA (b) the conversion reaction is carried out to convert the compound of Formula IB to the compound of Formula IIB:

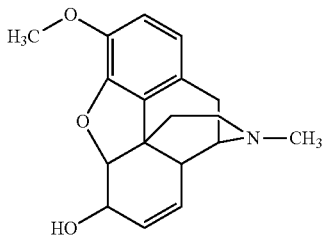

Formula IB

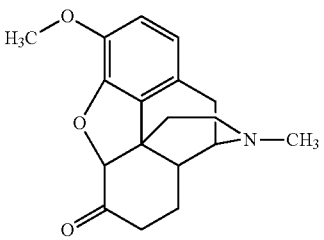

Formula IIB

5. The method of claim 1, wherein the non-supported heterogeneous ruthenium catalyst is chosen from elemental ruthenium; is in the form of ruthenium black; or is in the form of a ruthenium sponge; and the acid is chosen from sulfuric acid, alkyl sulfuric acid, aryl sulfuric acid, hydrochloric acid and acetic acid.

6. The method of claim 1, wherein the catalyst concentration in the reaction mixture is at least about 1 mole % and less than about 20 mole %, or at least about 5 mole % and less than about 15 mole %, or at least about 8 mole % and less than about 12 mole %, based on the amount of the compound of Formula I present therein; the reaction mixture contains between about 0.5 and about 3 moles, between about 0.75 and about 2.5 moles, or between about 1 and about 2 moles, of acid per mole of the compound of Formula I present therein; the reaction mixture is heated to a temperature of greater than about 25° C. and less than about 150° C., or greater than about 50° C. and less than about 120° C., or greater than about 75° C. and less than about 100° C.; and the conversion reaction is carried out for at least about 4 hours and less than about 24 hours, or at least about 8 hours and less than about 22 hours, or at least about 12 hours and less than about 20 hours.

7. The method of claim 1, wherein the reaction mixture additionally comprises a solvent selected from water, a water-miscible solvent, and mixtures thereof.

8. The method of claim 1, wherein the method further comprises:
  (i) isolating the non-supported, ruthenium metal catalyst from the reaction mixture;
  (ii) contacting the isolated, non-supported ruthenium metal catalyst with a solution in which the catalyst is at least partially soluble, in order to increase the activity of the catalyst; and,
  (iii) preparing a subsequent reaction mixture comprising the activated, non-supported catalyst and a compound of Formula I.

9. The method of claim 8, wherein less than about 15%, less than about 10%, less than about 5%, or less than about 1%, by weight of the isolated, non-supported ruthenium metal catalyst dissolves in the catalyst-soluble solution.

10. The method of claim 8, wherein the isolated, non-supported ruthenium metal catalyst is contacted with a solution having a hypochlorite concentration of from about 0.05 wt % to about 6 wt %, from about 0.1 wt % to about 4 wt %, or from about 0.5 wt % to about 2 wt %, based on the total weight of the solution.

11. The method of claim 8, wherein the isolated, non-supported ruthenium metal catalyst is contacted with the catalyst-soluble solution for at least about 30 seconds and less than about 10 minutes, or at least about 1 minute and less than about 8 minutes, or at least about 2 minutes and less than about 6 minutes, or at least about 3 minutes and less than about 5 minutes; the isolated, non-supported ruthenium metal catalyst is contacted with the catalyst-soluble solution at a temperature from about 0° C. to about 100° C., from about 5° C. to about 75° C., from about 15° C. to about 50° C., or at about room temperature; and the catalyst-soluble solution contains a base.

12. A method for preparing a compound of Formula IV from a compound of Formula III:

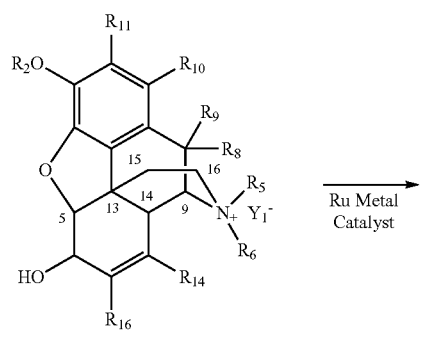

Formula III

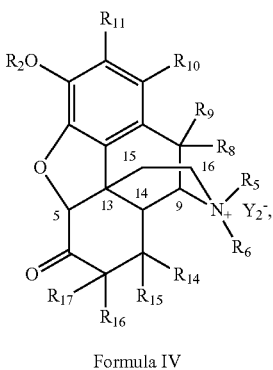

Formula IV the method comprising contacting the compound of Formula III with an acid and a non-supported, heterogeneous ruthenium metal catalyst in a reaction mixture to convert the compound of Formula III to the compound of Formula IV, wherein:

$R_2$ is chosen from hydrogen and substituted or unsubstituted alkyl, substituted or unsubstituted aryl, substituted or unsubstituted aryl alkyl, substituted or unsubstituted acyl, substituted or unsubstituted aryl sulfonyl, substituted or unsubstituted alkyl sulfonyl, substituted or unsubstituted carboxyester, substituted or unsubstituted carboxyamide, substituted or unsubstituted trialkylsilyl, and substituted or unsubstituted heterocycloalkyl;

$R_5$ and $R_6$ are independently chosen from hydrogen and substituted or unsubstituted alkyl, substituted or unsubstituted allyl, substituted or unsubstituted cycloalkyl, substituted or unsubstituted aryl, substituted or unsubstituted aryl alkyl, substituted or unsubstituted aryl sulfonyl, substituted or unsubstituted alkyl sulfonyl, substituted or unsubstituted acyl, substituted or unsubstituted formyl, hydroxyl, substituted or unsubstituted carboxyester and substituted or unsubstituted carboxyamide;

$R_8$ and $R_9$ are independently chosen from hydrogen, hydroxyl, substituted or unsubstituted hydrocarbyl, or $R_8$ and $R_9$ together form a carbonyl group;

$R_{10}$, $R_{11}$, $R_{14}$ and $R_{15}$ are independently chosen from hydrogen, substituted or unsubstituted hydrocarbyl, and a halogen, or $R_{14}$ and $R_{15}$ together form a carbonyl group;

$R_{16}$ and $R_{17}$ are independently chosen from hydrogen, substituted or unsubstituted hydrocarbyl, or $R_{16}$ and $R_{17}$ together form a carbonyl group; and, $Y_1$ and $Y_2$ are each an anion, which may be the same or different.

13. The method of claim 12, wherein $Y_1$ and $Y_2$ are independently selected from a halogen anion or an anion chosen from $H^-$, $BF_4^-$, $Pf_6^-$, $CHO_4^-$, $CHO_2^-$, $CF_3CO_2^-$, $CF_3SO_3^-$, $CH_3CO_2^-$, $ArCO_2^-$, $CH_3SO_3^-$, p-tolylSO$_3^-$, $HSO_4^-$, $H_2PO_4^-$ and $B(Ar)_4^-$.

14. The method of claim 12, wherein $R_2$ is chosen from hydrogen and methyl.

15. The method of claim 12, wherein the compounds of Formula III and IV are (+)-enantiomers, and the stereochemistry of the C(5), C(13), C(14), and C(9) carbons, respectively, of each compound is chosen from a combination listed in Table A, below, provided that the C(15) and the C(16) atoms are both either on the alpha face of the molecule or the beta face of the molecule:

TABLE A

| Combination | C5 | C13 | C14 | C9 |
|---|---|---|---|---|
| 1 | R | R | R | R |
| 2 | R | R | S | R |
| 3 | R | R | R | S |
| 4 | R | R | S | S |
| 5 | R | S | R | R |
| 6 | R | S | S | R |
| 7 | R | S | R | S |
| 8 | R | S | S | S |
| 9 | S | R | R | R |
| 10 | S | R | S | R |
| 11 | S | R | R | S |
| 12 | S | R | S | S |
| 13 | S | S | R | R |
| 14 | S | S | S | R |
| 15 | S | S | R | S |
| 16 | S | S | S | S |

16. The method of claim 12, wherein the non-supported heterogeneous ruthenium catalyst is chosen from elemental ruthenium; is in the form of ruthenium black; or is in the form of a ruthenium sponge; and the acid is chosen from sulfuric acid, alkyl sulfuric acid, aryl sulfuric acid, hydrochloric acid and acetic acid.

17. The method of claim 12, wherein the catalyst concentration in the reaction mixture is at least about 1 mole % and less than about 20 mole %, or at least about 5 mole % and less than about 15 mole %, or at least about 8 mole % and less than about 12 mole %, based on the amount of the compound of Formula III present therein; the reaction mixture contains between about 0.5 and about 3 moles, between about 0.75 and about 2.5 moles, or between about 1 and about 2 moles, of acid per mole of the compound of Formula III present therein; the reaction mixture is heated to a temperature of greater than about 25° C. and less than about 150° C., or greater than about 50° C. and less than about 120° C., or greater than about 75° C. and less than about 100° C.; and the conversion reaction is carried out for at least about 4 hours and less than about 24 hours, or at least about 8 hours and less than about 22 hours, or at least about 12 hours and less than about 20 hours.

18. The method of claim 12, wherein the method further comprises:
   (i) isolating the non-supported, ruthenium metal catalyst from the reaction mixture;
   (ii) contacting the isolated, non-supported ruthenium metal catalyst with a solution in which the catalyst is at least partially soluble, in order to increase the activity of the catalyst; and,
   (iii) preparing a subsequent reaction mixture comprising the activated, non-supported catalyst and a compound of Formula III.

19. The method of claim 18, wherein less than about 15%, less than about 10%, less than about 5%, or less than about 1%, by weight of the isolated, non-supported ruthenium metal catalyst dissolves in the catalyst-soluble solution.

20. The method of claim 18, wherein the isolated, non-supported ruthenium metal catalyst is contacted with a solution having a hypochlorite concentration of from about 0.05 wt % to about 6 wt %, from about 0.1 wt % to about 4 wt %, or from about 0.5 wt % to about 2 wt %, based on the total weight of the solution.

21. The method of claim 18, wherein the isolated, non-supported ruthenium metal catalyst is contacted with the catalyst-soluble solution for at least about 30 seconds and less than about 10 minutes, or at least about 1 minute and less than about 8 minutes, or at least about 2 minutes and less than about 6 minutes, or at least about 3 minutes and less than about 5 minutes; the isolated, non-supported ruthenium metal catalyst is contacted with the catalyst-soluble solution at a temperature from about 0° C. to about 100° C., from about 5° C. to about 75° C., from about 15° C. to about 50° C., or at about room temperature; and the catalyst-soluble solution contains a base.

* * * * *